(12) United States Patent
Fearnot et al.

(10) Patent No.: US 8,038,710 B2
(45) Date of Patent: Oct. 18, 2011

(54) ARTIFICIAL VALVE PROSTHESIS

(75) Inventors: Neal E. Fearnot, West Lafayette, IN (US); Alan R. Leewood, Lafayette, IN (US); Ram H. Paul, Jr., Bloomington, IN (US); Blayne A. Roeder, Lafayette, IN (US); William D. Voorhees, West Lafayette, IN (US)

(73) Assignees: Cook Medical Technologies LLC, Bloomington, IN (US); Med Institute, Inc., West Lafayette, IN (US)

( * ) Notice: Subject to any disclaimer, the term of this patent is extended or adjusted under 35 U.S.C. 154(b) by 207 days.

(21) Appl. No.: 11/807,879

(22) Filed: May 30, 2007

(65) Prior Publication Data
US 2007/0288087 A1     Dec. 13, 2007

Related U.S. Application Data

(60) Provisional application No. 60/809,201, filed on May 30, 2006.

(51) Int. Cl.
*A61F 2/24* (2006.01)

(52) U.S. Cl. .................. 623/2.17; 623/1.24; 623/2.12

(58) Field of Classification Search .............. 623/1.24, 623/2.36, 2.38, 2.17; 424/423; 606/151, 606/153
See application file for complete search history.

(56) References Cited

U.S. PATENT DOCUMENTS

| | | | |
|---|---|---|---|
| 4,675,361 A | 6/1987 | Ward et al. |
| 4,861,830 A | 8/1989 | Ward et al. |
| 4,902,508 A | 2/1990 | Badylak et al. |
| 5,017,664 A | 5/1991 | Grasel et al. |
| 5,405,381 A | 4/1995 | Olin |
| 5,413,599 A | 5/1995 | Imachi et al. |
| 5,554,389 A | 9/1996 | Badylak et al. |
| 5,589,563 A | 12/1996 | Ward et al. |
| 5,690,642 A | 11/1997 | Osborne et al. |
| 5,814,061 A | 9/1998 | Osborne et al. |
| 5,993,844 A | 11/1999 | Abraham et al. |
| 6,099,567 A | 8/2000 | Badylak et al. |
| 6,206,931 B1 | 3/2001 | Cook et al. |
| 6,287,334 B1 | 9/2001 | Moll et al. |
| 6,371,961 B1 | 4/2002 | Osborne et al. |
| 6,503,272 B2 | 1/2003 | Duerig et al. |
| 6,508,833 B2 | 1/2003 | Pavcnik et al. |
| 6,752,826 B2 | 6/2004 | Holloway et al. |
| 6,939,377 B2 | 9/2005 | Jayaraman et al. |

(Continued)

FOREIGN PATENT DOCUMENTS

FR       2788217       7/2000

(Continued)

OTHER PUBLICATIONS

PCT Search Report for PCT/US2007/012684.

(Continued)

*Primary Examiner* — Thomas J Sweet
*Assistant Examiner* — Seema Swaminathan
(74) *Attorney, Agent, or Firm* — Buchanan Nipper (57) ABSTRACT

A self-expanding or otherwise expandable artificial valve prostheses for deployment within a body passageway, such as a vessel or duct of a patient. The valve prostheses include a support structure having an outer frame, a supporting member and a valve leaflet. The portion of the valve leaflet is supported by the supporting member and is positioned away from the wall of the body passageway when the device is deployed within the body passageway.

20 Claims, 5 Drawing Sheets

U.S. PATENT DOCUMENTS

| | | | |
|---|---|---|---|
| 7,503,928 B2 * | 3/2009 | Case et al. | 623/1.24 |
| 2001/0007956 A1 | 7/2001 | Letac et al. | |
| 2001/0039450 A1 | 11/2001 | Pavcnik et al. | |
| 2002/0065552 A1 | 5/2002 | Jayaraman et al. | |
| 2002/0187288 A1 | 12/2002 | Lin et al. | |
| 2003/0014126 A1 | 1/2003 | Patel et al. | |
| 2003/0149471 A1 | 8/2003 | Briana et al. | |
| 2003/0236568 A1 * | 12/2003 | Hojeibane et al. | 623/1.24 |
| 2004/0019374 A1 * | 1/2004 | Hojeibane et al. | 623/1.13 |
| 2004/0034409 A1 | 2/2004 | Heublein et al. | |
| 2004/0073297 A1 | 4/2004 | Rohde et al. | |
| 2004/0180042 A1 | 9/2004 | Cook et al. | |
| 2004/0186558 A1 | 9/2004 | Pavcnik et al. | |
| 2004/0225352 A1 | 11/2004 | Osborne et al. | |
| 2004/0260389 A1 * | 12/2004 | Case et al. | 623/1.24 |
| 2004/0260390 A1 | 12/2004 | Sarac et al. | |
| 2004/1026039 | 12/2004 | Sarac et al. | |
| 2005/0096735 A1 | 5/2005 | Hojeibane et al. | |
| 2006/0265053 A1 | 11/2006 | Hunt | |
| 2007/0027535 A1 | 2/2007 | Purdy et al. | |
| 2007/0093887 A1 * | 4/2007 | Case et al. | 623/1.24 |
| 2007/0129788 A1 * | 6/2007 | Drasler et al. | 623/1.24 |
| 2007/0185565 A1 * | 8/2007 | Schwammenthal et al. | 623/1.24 |
| 2010/0204781 A1 * | 8/2010 | Alkhatib | 623/1.26 |

FOREIGN PATENT DOCUMENTS

| | | |
|---|---|---|
| FR | A-2788217 | 7/2000 |
| WO | WO 01/28459 A1 | 4/2001 |
| WO | WO0128459 | 4/2001 |
| WO | WO 03/002165 A1 | 1/2003 |
| WO | WO 03/047468 A1 | 6/2003 |
| WO | WO03047468 | 6/2003 |
| WO | WO 2004/080352 A1 | 9/2004 |
| WO | WO 2004/089253 A1 | 10/2004 |

OTHER PUBLICATIONS

European Patent Office, Examiner's Report, Mar. 2, 2011 for Eurpoean patent application No. 07795464.2.

Canadian Intellectual Property Office, Examiner's Report, Mar. 24, 2011 for Canadian patent application No. 2,653,913.

Canadian Intellectual Property Office, Examiner's Report for Canadian application No. 2,653,913, Jul. 26, 2010.

* cited by examiner

ARTIFICIAL VALVE PROSTHESIS

RELATED APPLICATIONS

This non-provisional patent application claims priority to U.S. Provisional Patent Application No. 60/809,201, filed May 30, 2006, the contents of which are incorporated by reference in their entirety.

TECHNICAL FIELD

This invention relates to medical devices, more particularly to artificial valve prostheses and the like.

BACKGROUND

Many vessels in animals transport fluids from one bodily location to another. In some vessels, such as mammalian veins, natural valves are positioned along the length of the vessel to permit fluid flow in a substantially unidirectional manner along the length of the vessel. These natural valves are particularly important in the lower extremities to prevent blood from pooling in the lower legs and feet during situations, such as standing or sitting, when the weight of the column of blood in the vein can act to prevent positive blood flow toward the heart. A condition, commonly known as "chronic venous insufficiency", is primarily found in individuals where gradual dilation of the veins, thrombotic events, or other conditions prevent the leaflets of the native valves from closing properly. This leads to significant leakage of retrograde flow such that the valve is considered "incompetent". Chronic venous insufficiency is a potentially serious condition in which the symptoms can progress from painful edema and unsightly spider or varicose veins to skin ulcerations. Elevation of the feet and compression stockings can relieve symptoms, but do not treat the underlying disease. Untreated, the disease can impact the ability of individuals to maintain their normal lifestyle.

To treat venous valve insufficiency, a number of surgical procedures have been employed to improve or replace the native valve, including placement of artificial valve prostheses. These efforts have met with limited success and have not been widely adopted as methods of treating chronic venous insufficiency. More recently, efforts have been directed towards finding a suitable self-expanding or radially-expandable artificial valve prostheses that can be placed using minimally invasive techniques, rather than requiring open surgery and its obvious disadvantages. Thus far, use of prosthetic venous valves has remained experimental only.

Prosthetic valves have been developed that use a support frame such as a stent. Frequently, a graft member is attached to the support frame and provides a valve function to the device. For example, the graft member can be in the form of a leaflet that is attached to a stent and movable between first and second positions. In a first position, the valve is open and allows fluid flow to proceed through a vessel in a first direction, and in a second position the valve is closed to restrict fluid flow in a second, opposite direction. Examples of such prosthetic valves are described in commonly owned U.S. Pat. No. 6,508,833, filed Mar. 21, 2001, and U.S. Publication No. 2004/0186558, published Sep. 23, 2004. Another example of a prosthetic valve assembly, including a valve seat and a movable valve composed of a flexible member, is provided by U.S. Pat. No. 5,413,599, filed Dec. 13, 1999.

Prosthetic valves are designed to replace or supplement the function of incompetent natural valves. The use of an expandable support frame in valve devices allows for the use of minimally invasive delivery devices and techniques for placement of the valves within body vessels, which will likely lower the overall cost of treatment and increase the acceptance of these medical devices by practitioners and patients alike. Drawbacks of current prosthetic valves include thickening of the valve leaflet material, often leading to a deterioration of valve function over time. Also, the natural variation in the diameter of mammalian vessels sometimes results in a valve prosthesis being positioned within a vessel of a smaller dimension than is optimum for that valve.

SUMMARY

The present invention provides artificial valve prostheses, such as artificial venous valves, having a valve structure and a self-expanding or otherwise expandable support structure. The valve prostheses are constructed so as to allow fluid flow in a first, antegrade, direction and to restrict fluid flow in a second, retrograde, direction.

In one embodiment, the valve prosthesis includes an outer frame and an attached first support element extending, in the direction of antegrade flow, into a lumen formed by the outer frame. A first valve leaflet is supported by the outer frame and by the first support element with a portion of the perimeter of the first valve leaflet attached to the first support element. The first valve leaflet is deformable between a first position allowing fluid flow in the first, antegrade, direction and a second position restricting fluid flow in a second, retrograde, direction.

In another embodiment, the valve prosthesis further includes a second valve leaflet also supported by the outer frame and by the first support element. The valve leaflets are attached at a first commissural point on the first support element and at a second commissural point and have a co-apting edge between the commissural points. The second commissural point can be positioned on the outer frame.

In yet another embodiment, the valve prosthesis includes a second support element attached to the outer frame. The second commissural point can be positioned on the second support element.

Another aspect of the present invention provides a method of regulating fluid flow within a body vessel. The method includes delivering an artificial valve prosthesis of the present invention within a lumen of a catheter to a position within the vessel and deploying the artificial valve prosthesis from the lumen.

Yet another aspect of the present invention provides a medical device including a catheter and an artificial valve prosthesis of the present invention positioned within a lumen of the catheter in a compressed configuration.

BRIEF DESCRIPTION OF THE DRAWINGS

Embodiments of the present invention will now be described by way of example with reference to the accompanying drawings.

FIGS. 3(a), (b) and (c) are schematic views of yet another illustrative embodiment of the present invention. FIG. 3(b) depicts another valve prosthesis having a support frame supporting two valve leaflets formed from a continuous membrane in the form of a cone structure.

FIGS. 5(a) and 5(b) are schematic plan views of a valve prosthesis having three valve leaflets.

DETAILED DESCRIPTION

Definitions

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. The materials, methods, and examples disclosed herein are illustrative only and not intended to be limiting.

The term "implantable" refers to an ability of a medical device to be positioned at a location within a body, such as within a body vessel. Furthermore, the terms "implantation" and "implanted" refer to the positioning of a medical device at a location within a body, such as within a body vessel.

An "alloy" is a substance composed of two or more metals or of a metal and a nonmetal united, such as by chemical or physical interaction. Alloys can be formed by various methods, including being fused together and dissolving in each other when molten, although molten processing is not a requirement for a material to be within the scope of the term "alloy." As understood in the art, an alloy will typically have physical or chemical properties that are different from its components.

A "biodegradable" material is a material that dissipates upon implantation within a body, independent of the mechanisms by which dissipation can occur, such as dissolution, degradation, absorption and excretion. The actual choice of which type of materials to use may readily be made by one of ordinary skill in the art. Such materials are often referred to by different terms in the art, such as "bioresorbable," "bioabsorbable," or "biodegradable," depending upon the mechanism by which the material dissipates. The prefix "bio" indicates that the erosion occurs under physiological conditions, as opposed to other erosion processes, caused for example, by high temperature, strong acids or bases, UV light or weather conditions.

A "biocompatible" material is a material that is compatible with living tissue or a living system by not being toxic or injurious and not causing immunological rejection.

A "non-bioabsorbable" or "biostable" material refers to a material, such as a polymer or copolymer, which remains in the body without substantial dissipation.

A "remodelable material" is a material that, when implanted in vivo, is capable of being resorbed by the body or providing a matrix for the regrowth of autologous cells. In some embodiments, fluid contacting autologous cells on an implanted remodelable material interface can affect the growth of autologous tissue on the implanted remodelable material.

The phrase "controlled release" refers to the release of an agent at a predetermined rate. A controlled release may be constant or vary with time. A controlled release may be characterized by a drug elution profile, which shows the measured rate that the agent is removed from a device in a given solvent environment as a function of time. For example, a controlled release elution profile from a valve prosthesis may include an initial burst release associated with the deployment of the valve prosthesis, followed by a more gradual subsequent release. A controlled release may be a gradient release in which the concentration of the agent released varies over time or a steady state release in which the agent is released in equal amounts over a certain period of time (with or without an initial burst release).

As used herein, the phrase "bioactive agent" refers to any pharmaceutically active agent that produces an intended therapeutic effect on the body to treat or prevent conditions or diseases.

As used herein, a "venous valve-related condition" is any condition presenting symptoms that can be diagnostically associated with improper function of one or more venous valves. In mammalian veins, venous valves are positioned along the length of the vessel in the form of leaflets disposed annularly along the inside wall of the vein which open to permit blood flow toward the heart and close to prevent back flow. Two examples of venous valve-related conditions are chronic venous insufficiency and varicose veins.

Implantable Valve Prostheses

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

Devices and systems of the invention are desirably adapted for deployment within a body lumen, and in particular embodiments, devices and systems of the invention are adapted for deployment within the venous system. Accordingly, preferred devices adapted are venous valves, for example, for percutaneous implantation within veins of the legs or feet to treat venous insufficiency. However, devices and systems of the present invention may be adapted for deployment within any tube-shaped body passage lumen that conducts fluid, including but not limited to blood vessels, such as those of the human vasculature system; billiary ducts; ureteral passages and the alimentary canal.

One aspect of the present invention provides a self-expanding or otherwise expandable artificial valve prosthesis for deployment within a bodily passageway, such as a vessel or duct of a patient. The prosthesis is typically delivered and implanted using well-known transcatheter techniques for self-expanding or otherwise expandable prostheses. The valve prosthesis is positioned so as to allow antegrade fluid flow and to restrict retrograde fluid flow. Antegrade fluid flow travels from the distal (upstream) end of the prosthesis to the proximal (downstream) end of the prosthesis, the latter being located closest to the heart in a venous valve when placed within the lower extremities of a patient. Retrograde fluid flow travels from the proximal (downstream) end of the prosthesis to the distal (upstream) end of the prosthesis The valve prostheses of the present invention are configured to address shortcomings of prior expandable valve prostheses. One such shortcoming occurs when regions of the leaflets, particularly those regions close to the commissural points, are in contact with the wall of the vessel. This interaction can result in a thickening of the leaflet material, leading to deterioration in leaflet flexibility over time. Such a reduction in flexibility can cause a reduction in valve performance.

Another shortcoming occurs when the expandable valve prosthesis is oversized in relation to the diameter of the body lumen into which it is placed. As a result, the valve prosthesis cannot expand to its intended radial diameter. If the valve leaflets are attached to the partially expanded support frame, the distance between the commissural points defining the opening between the valve leaflets may not be sufficiently large to allow the valve leaflets to properly seal along their co-apting edges in response to retrograde flow. Consequentially, the valve prosthesis may not restrict retrograde flow to the required extent.

Finally, if the edges of the valve leaflets are attached to the support frame, any shrinkage of the leaflet material will tend to result in tearing of the leaflet because the support frame does not contract to accommodate such shrinkage.

Figure 1:
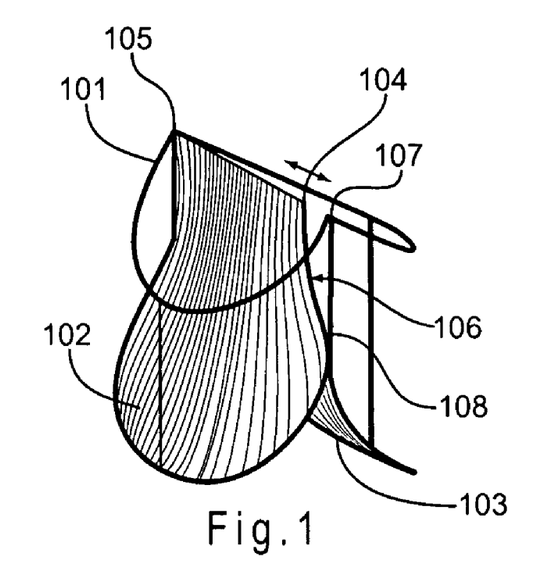
FIG. 1 is a schematic view of an illustrative embodiment of the present invention and depicts a valve prosthesis having two valve leaflets and one support element.

FIG. 1 illustrates one embodiment of the present invention. In this embodiment, support frame 101 and attached support element 106 support valve leaflets 102 and 103 that co-apt between two commissural points 104 and 105. Commissural point 104 is positioned on support element 106, while commissural point 105 is positioned on support frame 101. Support element 106 extends from an attachment point 108 on support frame 101 into the lumen formed by the expanded frame. The regions of the perimeter of valve leaflets 102 and 103 that are attached to support element 106 are positioned away from the vessel wall.

In one embodiment, support element 106 accommodates limited radial movement of commissural point 104 with respect to support frame 101. For example, support element 106 can be flexible itself or can be attached to support frame 101 by a flexible join. For example, the join may include a coil or a fillet, although a simple bend may offer superior fatigue life for some materials. Example of frames having such joins may be found in U.S. Publication No. 2004/0186558, published Sep. 23, 2004, the contents of which are incorporated by reference. Such a configuration allows support element 106 to accommodate sealing along the co-apting edges of valve leaflets 102 and 103, when subjected to retrograde flow, even when the fully expanded radial diameter of support frame 101 is slightly oversized relative to the body vessel in which the valve prosthesis is placed. In such a situation, commissural point 104 is free to move radially towards point 107 on support frame 101. Alternatively, shrinkage of the leaflet material may be accommodated for by movement of commissural point 104 away from point 107 on support frame 101. In any case, support element 106 is itself sufficiently rigid and is attached to support frame 101 in such a way that it maintains sufficient rigidity to prevent the collapse of valve leaflets 102 and 103.

Figure 2:
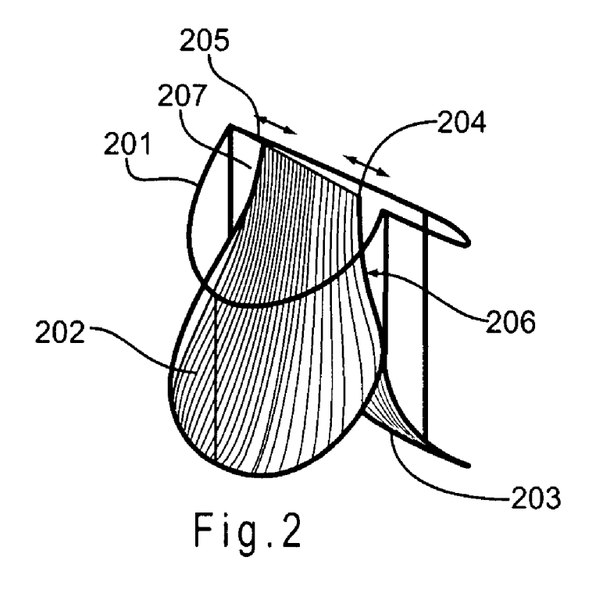
FIG. 2 is a schematic view of another illustrative embodiment of the present invention and depicts a valve prosthesis having two valve leaflets and two support elements.

FIG. 2 shows another illustrative embodiment of the present invention. Support frame 201 and support elements 206 and 207 support valve leaflets 202 and 203 that co-apt between two commissural points 204 and 205. Commissural point 204 is positioned on support element 206 and commissural point 205 is positioned on support element 207. In this embodiment, the regions of valve leaflets 202 and 203 that are attached to support elements 206 and 207 are positioned away from the vessel wall.

In one embodiment, support elements 206 and 207 are sufficiently flexible, or are attached to support frame 201 by flexible joins, so as to allow for the sealing along the co-apting edges of valve leaflets 202 and 203, when subjected to retrograde flow, even when the fully expanded radial diameter of support frame 201 is slightly oversized relative to the body lumen in which the valve prosthesis is placed. In such an embodiment, support elements 206 and 207 position commissural points 204 and 205 closer to support frame 201 than is the case when support frame 201 is expanded to its full radial dimension.

Figure 3A:
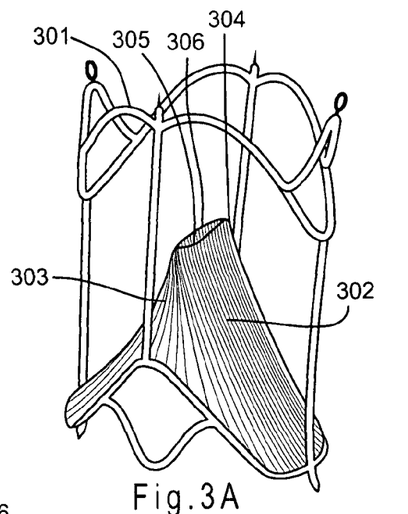
FIG. 3(a) depicts a valve prosthesis having a support frame supporting two valve leaflets formed from a continuous membrane in the form of a cone structure. The cone structure tapers towards the downstream end of the valve prosthesis and terminates at two co-apting edges.

FIG. 3(a) shows yet another illustrative embodiment of a valve prosthesis of the present invention. Support frame 301 supports two valve leaflets formed from a continuous membrane 302 in the form of a cone structure that attaches to support frame 301 towards the upstream end of the valve prosthesis. The cone structure tapers towards the downstream end of the valve prosthesis and terminates at two co-apting edges 305 and 306. The length of these edges is shorter that the expanded diameter of the support frame. In one embodiment, reinforced portions 303 and 304 may be incorporated into the cone structure to help support the cone structure and prevent prolapse.

Figure 3B:
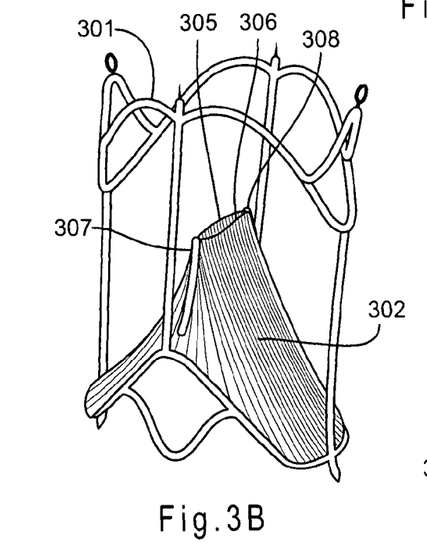
FIG. 3(b) depicts a valve prosthesis having a support frame supporting two valve leaflets formed from a continuous membrane in the form of a cone structure. The cone structure is supported by two support elements and tapers towards the downstream end of the valve prosthesis and terminates at two co-apting edges.

FIG. 3(b) shows yet another illustrative embodiment of the valve prosthesis of the present invention. Here, the cone structure 302 is supported by support elements 307 and 308. In this embodiment, support elements 307 and 308 do not attach to support structure 301. Again, the length of co-apting edges 305 and 306 is shorter that the expanded diameter of the support frame.

Figure 3C:
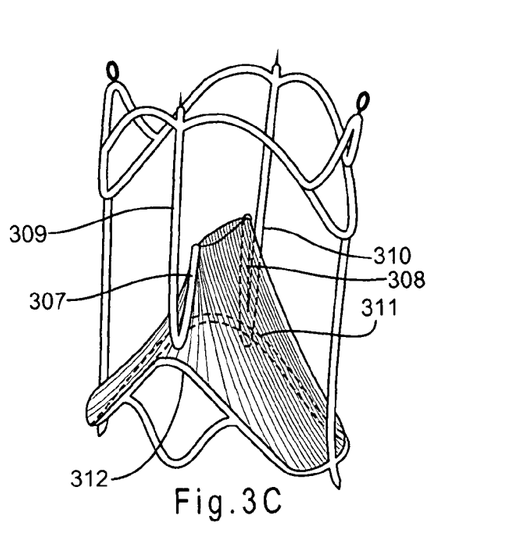

FIG. 3(c) shows another illustrative embodiment. In this embodiment, support elements 307 and 308 attach to support frame members 309 and 310 respectively but not to support frame members 311 and 312.

Figure 4:
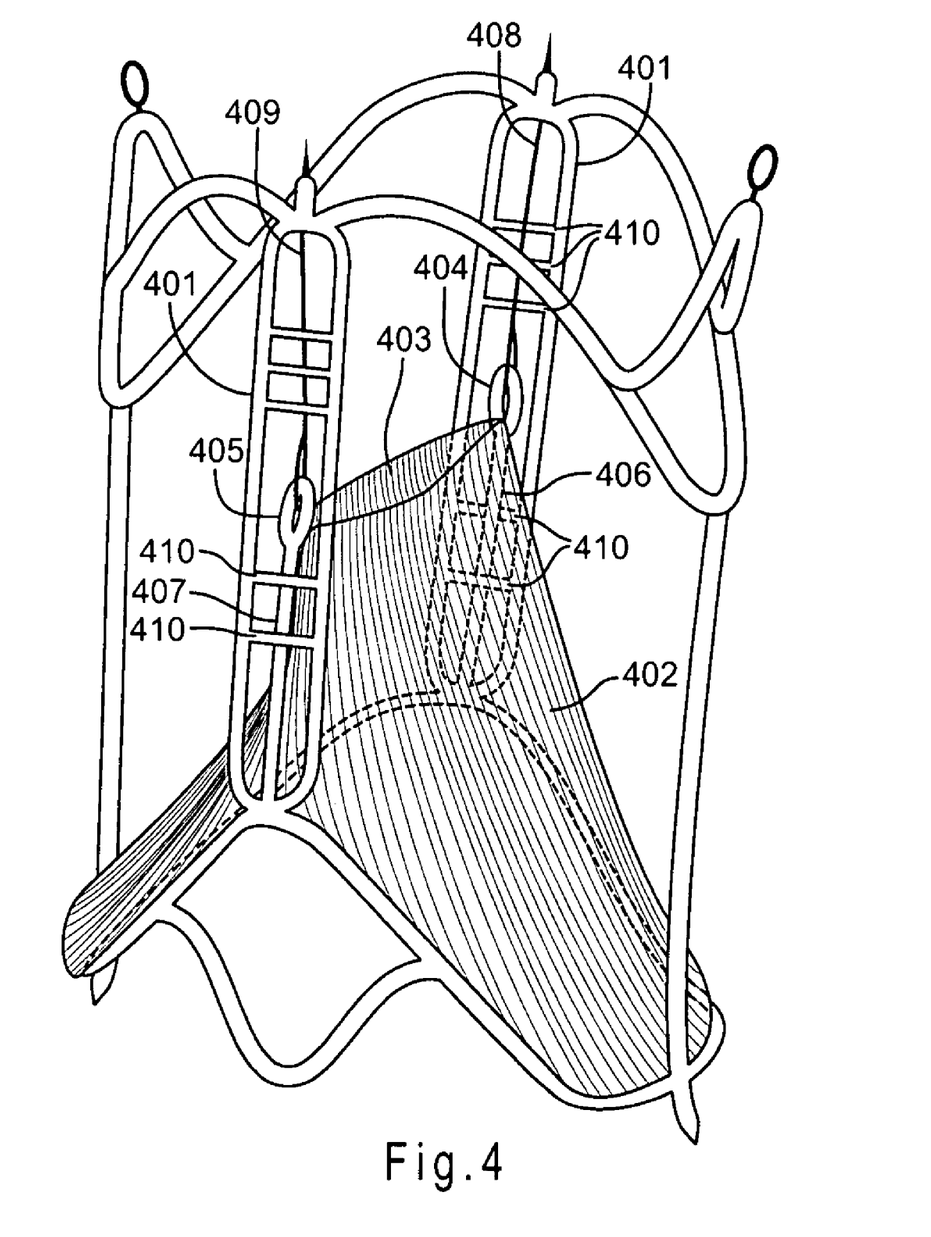
FIG. 4 is a schematic view of another illustrative embodiment of a valve prosthesis the present invention.

FIG. 4 shows an illustrative embodiment of the present invention in which support elements 406 and 407 are additionally supported by elements 408 and 409 respectively. For example, elements 408 and/or 409 may be sutures. Support elements 406 and 407 may contain eyelets 404 and 405 to provide anchoring points for the sutures. Alternatively, elements 408 and 409 may be similar to support elements 406 and 407. In one embodiment, support frame 401 may include rib elements 410. Such elements limit or prevent the collapse of the vessel wall through the support frame onto support elements 406 and 407 and valve leaflets 402 and 403.

Figure 5A:
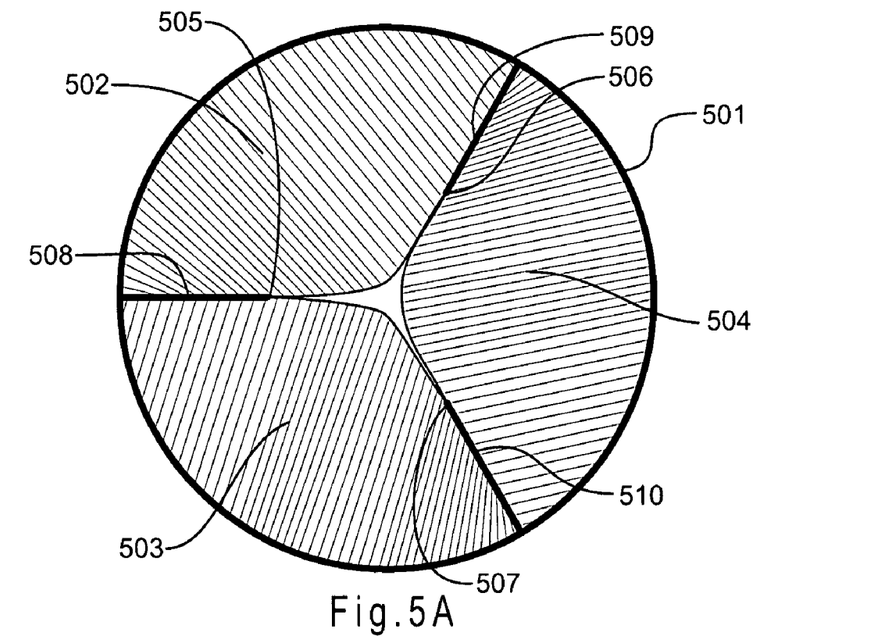
FIG. 5(a) depicts a valve prosthesis having leaflets positioned by retrograde flow.
Figure 5B:
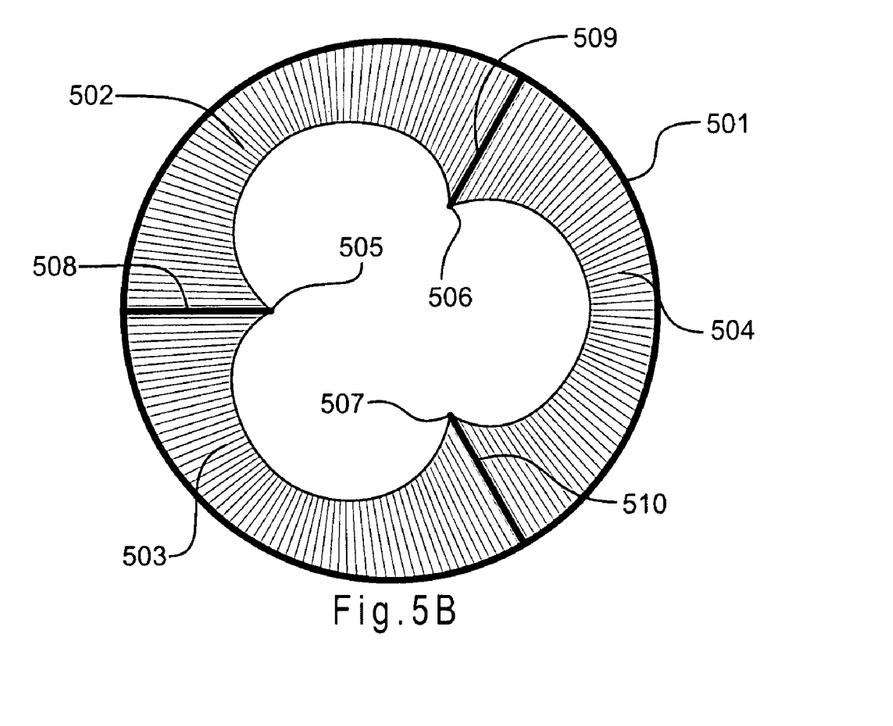
FIG. 5(b) depicts a valve prosthesis having leaflets positioned by antegrade flow.

FIGS. 5(a) and (b) shows a plan view of another illustrative embodiment of the present invention. Support frame 501 and support elements 508, 509 and 510 support three valve leaflets 502, 503 and 504 that co-apt between three commissural points 505, 506 and 507. The regions of the perimeter of the valve leaflets supported by support elements 508, 509 and 510 are again positioned away from the vessel wall. FIG. 5(a) shows the valve leaflets restricting retrograde flow while FIG. 5(b) shows the valve leaflets positioned in an open position by antegrade flow.

In the above embodiments, the amount of slack in the valve leaflet material determines, at least in part, how well the valve leaflets restrict retrograde flow and how large of an opening they permit during antegrade flow. In one embodiment, the valve prosthesis is configured such that, when the valve leaflets are positioned in their fully open position by antegrade flow, the cross sectional area available for fluid flow is between 90 and 10 percent of the cross sectional area of the expanded outer frame in the region of attachment of the valve leaflets to the support frame. In another embodiment, the valve prosthesis is configured such that the cross sectional area available for antegrade fluid flow is between 70 and 30 percent of the cross sectional area of the expanded outer frame in the region of attachment of the valve leaflets to the support frame. In yet another embodiment, the valve prosthesis is configured such that the cross sectional area available for antegrade fluid flow is between 50 and 40 percent of the cross sectional area of the expanded outer frame in the region of attachment of the valve leaflets to the support frame.

Elements shown in the embodiments described herein can be added to and/or exchanged with other embodiments to provide additional embodiments. It will also be understood that other valve body configurations are also contemplated as being within the scope of the present invention. For example, valves having four or more valve leaflets are contemplated. Hence, the number of leaflets possible for embodiments of the present invention can be one, two, three, four, five or any practical number. Bi-leaflet valves are preferred in low-flow venous situations. The valve leaflets may be of equal size and shape or of differing size and shape depending on the configuration of the supporting frame members.

Valve Prosthesis Support Frame

The support frame used in the artificial valve prosthesis of the present invention can be, for example, formed from wire, cut from a section of cannula, molded or fabricated from a polymer, biomaterial, or composite material, or a combination thereof. The pattern (i.e., configuration of struts and cells) of the outer frame, including any anchoring portion(s), which is selected to provide radial expandability to the prosthesis is also not critical for an understanding of the invention. Any support frame is applicable for use with the claimed valve prosthesis so long as this structure allows the valve leaflets to be supported in the required position and allows the required portion of the perimeter of the leaflet to remain away from the vessel wall. Numerous examples of support structures are disclosed in U.S. Patent Publication No. 2004/01866558A1, published Sep. 23, 2004, the contents of which are incorporated herein by reference.

Figure 6:
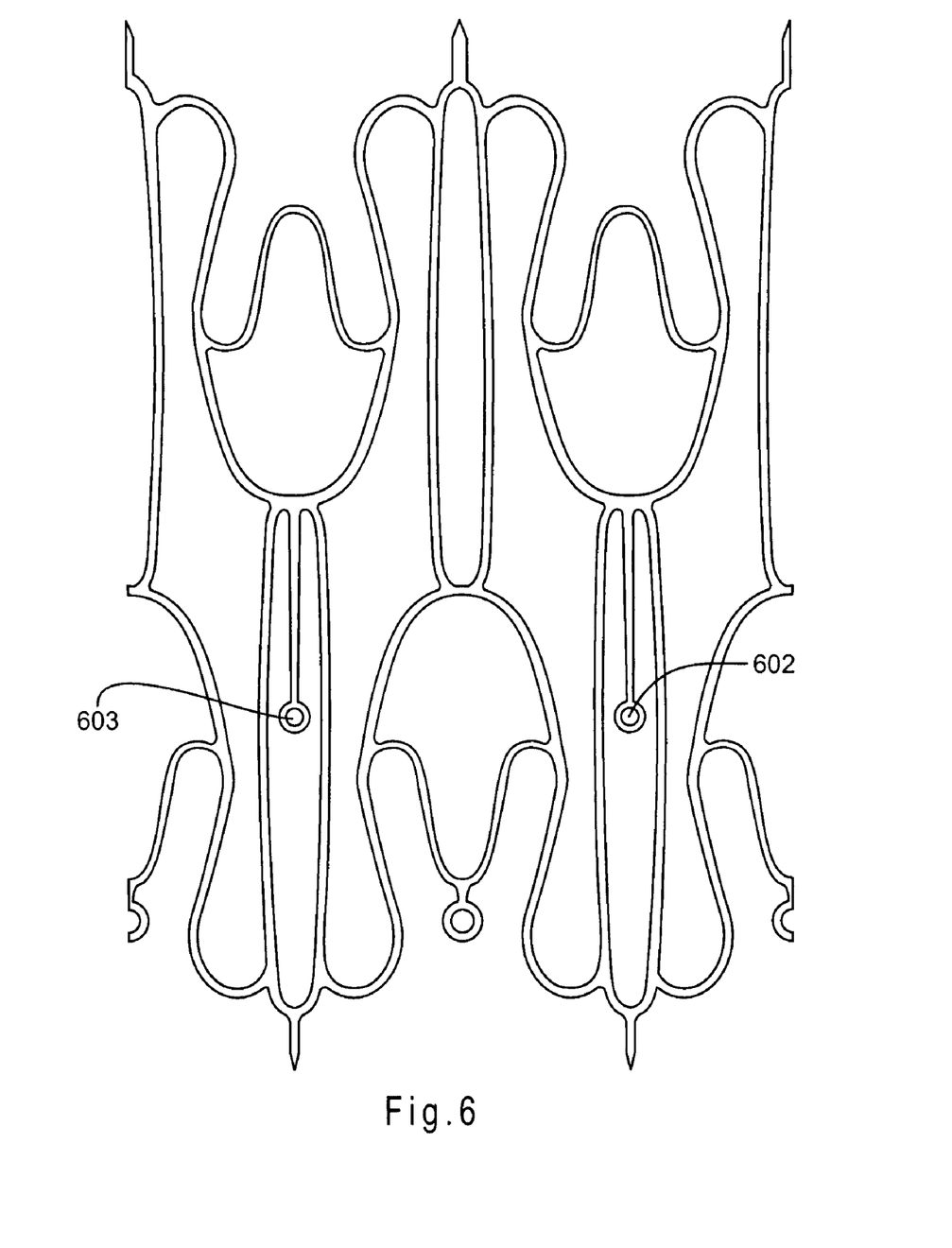
FIG. 6 is a schematic view of another illustrative embodiment of a valve prosthesis the present invention.

For example, FIG. 6 illustrates flattened view of a support frame suitable for use in the present invention. The figure shows a view of a support structure similar to that shown in FIG. 4 with support elements 602 and 603 continuous with the main body of the support frame. Such a support frame may be cut, for example by laser cutting from a hollow tube of material.

Reduction in Valve Leaflet-Vessel Wall Interaction

The artificial valve prosthesis of the present invention allows for the positioning of a portion of the perimeter of one or more valve leaflets away from the vessel wall. In such embodiments, a portion of at least one valve leaflet is supported by a support element that extends into the lumen of the vessel into which the valve prosthesis is placed.

For example, if the support frame and support element are made of a self-expanding memory material (discussed below), the frame can be constructed so that the support element extends into the vessel lumen when the frame expands to its programmed state. Alternatively, the support element may be manufactured from a material such as stainless steel and attached to the support frame at such an angle that the support element extends into the lumen of the vessel when the support frame expands.

In one embodiment, the length of the support element(s) is such that at least 10% of the attached portion of the perimeter of a valve leaflet is attached to the supporting member(s) and is positioned away from the vessel wall. The attached portion of the perimeter of the valve leaflet is that portion of the perimeter that is attached to the supporting member(s) or other portions of the support frame and does not include the co-apting portion of the perimeter of the valve leaflet between the commissural points.

In another embodiment, the length of the support element(s) is such that at least 25% of the attached portion of the perimeter of a valve leaflet is attached by the supporting member(s). In another embodiment, the length of the support element(s) is such that at least 40% of the attached portion of the perimeter of a valve leaflet is attached by the supporting member(s). In other embodiments, the length of the support element(s) is such that at least 50%, 70%, 80% or 90% of the attached portion of the perimeter of a valve leaflet is attached by the supporting member(s).

Accommodation of Oversized Deployment

The artificial valve prosthesis of the present invention may be configured to accommodate deployment of an oversized valve prosthesis within a vessel. As was discussed above, when deployed within a vessel having a diameter smaller than that required to allow full expansion of the valve prosthesis, the valve leaflets may be deployed so that the distance between the commissural points is less than is optimal to allow for proper sealing of the leaflets during retrograde flow.

In one embodiment, the valve prosthesis accommodates deployment within a vessel that allows only partial expansion of the valve prosthesis, such that the diameter of the partially expanded valve prosthesis is up to 6 mm less than its fully expanded diameter. In another embodiment, the valve prosthesis accommodates deployment within a vessel that allows only partial expansion of the valve prosthesis, such that the diameter of the partially expanded valve prosthesis is up to 4 mm less than its fully expanded diameter. In yet another embodiment, the valve prosthesis accommodates deployment within a vessel that allows only partial expansion of the valve prosthesis, such that the diameter of the partially expanded valve prosthesis is up to 2 mm less than its fully expanded diameter.

The ability of the valve prosthesis to accommodate deployment within a vessel that allows only partial expansion of the valve prosthesis is determined by factors including the length of the support element, the flexibility of the support element and the angle of attachment of the support element to the outer frame.

Controlled Retrograde Flow

The artificial valve prosthesis of the present invention can be configured to permit a controlled amount of retrograde flow through a body vessel despite the presence of the valve prosthesis. This may be desirable for a variety of reasons. For example, a controlled amount of retrograde flow can assist in the prevention of pooling of fluid when the valve prosthesis is in a closed or substantially closed configuration in the body vessel.

Any suitable means for permitting a controlled amount of retrograde flow to pass through the valve prosthesis can be used in any of the embodiments described herein. For example, the present invention contemplates valve prostheses having at least one valve leaflet including one or more apertures in the body of the valve leaflet.

The aperture can have any suitable shape. Examples of specifically contemplated shapes include circular, ovoid, triangular, square, rectangular, and tear-drop shaped openings. Furthermore, multiple openings can be used. In these embodiments, the sum total open area of all openings is advantageously in accordance with the parameters described above. Further examples of valves having apertures allowing limited retrograde flow are disclosed in U.S. Publication No.

2004/0225352A1, published Nov. 11, 2004, the contents of which are incorporated herein by reference.

Frame Composition

The materials used in the support frame and the support elements supporting the valve leaflets, can be selected from a well-known list of suitable metals and polymeric materials appropriate for the particular application, depending on necessary characteristics that are required, for example, self-expansion, high radial force, collapsibility, etc. Suitable metals or metal alloys include stainless steels (e.g., 316, 316L or 304); nickel-titanium alloys including shape memory or superelastic types (e.g., nitinol or elastinite); inconel; noble metals including copper, silver, gold, platinum, palladium and iridium; refractory metals including molybdenum, tungsten, tantalum, titanium, rhenium, or niobium; stainless steels alloyed with noble and/or refractory metals; magnesium; amorphous metals; plastically deformable metals (e.g., tantalum); nickel-based alloys (e.g., including platinum, gold and/or tantalum alloys); iron-based alloys (e.g., including platinum, gold and/or tantalum alloys); cobalt-based alloys (e.g., including platinum, gold and/or tantalum alloys); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; platinum-iridium alloys; platinum-tungsten alloys; magnesium alloys; titanium alloys (e.g., TiC, TiN); tantalum alloys (e.g., TaC, TaN); L605; magnetic ferrite; bioabsorbable materials, including magnesium; or other biocompatible metals and/or alloys thereof.

In various embodiments, the support frame includes a metallic material selected from stainless steel, nickel, silver, platinum, palladium, gold, titanium, tantalum, iridium, tungsten, a self-expanding nickel-titanium alloy, a super elastic nickel-titanium alloy sold under the tradename NITINOL or inconel.

One particularly preferred material for forming the support frame is a self-expanding material such as the superelastic nickel-titanium alloy NITINOL. Materials having superelastic properties generally have at least two phases a martensitic phase, which has a relatively low tensile strength and which is stable at relatively low temperatures, and an austenitic phase, which has a relatively high tensile strength and which can be stable at temperatures higher than the martensitic phase. Shape memory alloys undergo a transition between an austenitic phase and a martensitic phase at certain temperatures. When they are deformed while in the martensitic phase, they retain this deformation as long as they remain in the same phase, but revert to their original configuration when they are heated to a transition temperature, at which time they transform to their austenitic phase. The temperatures at which these transitions occur are affected by the nature of the alloy and the condition of the material. Nickel-titanium-based alloys (NiTi), wherein the transition temperature is slightly lower than body temperature, are preferred for the present invention. It can be desirable to have the transition temperature set at just below body temperature to insure a rapid transition from the martinsitic state to the austenitic state when the frame can be implanted in a body lumen.

Preferably, the support frame comprises a self-expanding nickel titanium (NiTi) alloy material. NITINOL is a suitable self-expanding material that can be deformed by collapsing the frame and creating stress which causes the NiTi to reversibly change to the martensitic phase. The support frame can be restrained in the deformed condition inside a delivery sheath typically to facilitate the insertion into a patient's body, with such deformation causing the isothermal phase transformation. Once within the body lumen, the restraint on the support frame can be removed, thereby reducing the stress thereon so that the superelastic support structure returns towards its original undeformed shape through isothermal transformation back to the austenitic phase. Other shape memory materials may also be utilized, such as, but not limited to, irradiated memory polymers such as autocrosslinkable high density polyethylene (HDPEX). Shape memory alloys are known in the art and are discussed in, for example, "Shape Memory Alloys," Scientific American, 281: 74-82 (November 1979).

Some embodiments provide support frames that are not self-expanding, or that do not comprise superelastic materials. For example, in other embodiments, the support frame can comprise silicon-carbide (SiC). For example, published U.S. Publication No. 2004/034409A1, published Feb. 14, 2004 and incorporated in its entirety herein by reference, discloses various suitable frame materials and configurations.

Other suitable materials used in the support frame include carbon or carbon fiber, cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, polylactic acid, polyglycolic acid, a polyanhydride, polycaprolactone, polyhydroxybutyrate valerate, a biodegradable polymeric material, a biocompatible polymeric material, a protein, an extracellular matrix component, collagen, fibrin, a biologic agent, or a suitable mixture or copolymer of any of these.

Valve Leaflet Composition

The material used in body of the valve leaflets includes a biocompatible material, and is, in one embodiment, a bioremodelable material. Suitable bioremodelable materials may be made from natural or synthetic polymers, including collagen. Thus, in general, the flexible material may comprise a synthetic biocompatible polymer such as cellulose acetate, cellulose nitrate, silicone, polyethylene, teraphthalate, polyurethane, polyamide, polyester, polyorthoester, poly anhydride, polyether sulfone, polycarbonate, polypropylene, high molecular weight polyethylene, a fluoroplastic material such as polytetrafluoroethylene, polylactic acid, polyglycolic acid or copolymers thereof, a polyanhydride, polycaprolactone, polyhydroxy-butyrate valerate, polyhydroxyalkanoate, a biodegradable polymer or mixtures or copolymers thereof.

In certain embodiments of the invention, the flexible material is comprised of a naturally derived or synthetic collagenous material, and especially an extracellular collagen matrix material. Suitable extracellular matrix materials ("ECM material") include, for instance, submucosa (including, for example, small intestinal submucosa ("SIS"), stomach submucosa, urinary bladder submucosa, or uterine submucosa), renal capsule membrane, dura mater, pericardium, serosa, and peritoneum or basement membrane materials, including liver basement membrane. These layers may be isolated and used as intact natural sheet forms, or reconstituted collagen layers including collagen derived from these materials or other collagenous materials may be used. For additional information as to submucosa materials useful in the present invention, and their isolation and treatment, reference can be made to U.S. Pat. Nos. 4,902,508, 5,554,389, 5,993,844, 6,206,931, and 6,099,567, the contents of which are incorporated herein by reference. Renal capsule tissue can also be obtained from warm blooded vertebrates, as described more particularly in U.S. Publication No. 2003/0014126A1, published Jan. 16, 2003, and International Patent Application Serial No. PCT/US02/20499, filed Jun. 28, 2002, and published Jan. 9, 2003 as International Publication No. WO03002165, the contents of which are incorporated herein by reference.

In one embodiment, the ECM material is porcine SIS. SIS can be prepared according to the method disclosed in U.S. Publication No. 2004/0180042A1, published Sep. 16, 2004, the contents of which are incorporated herein by reference.

In certain embodiments of the invention, the valve leaflet material is a biocompatible polyurethane. One example of a biocompatible polyurethane is THORALON (THORATEC, Pleasanton, Calif.). THORALON is described in U.S. Pat. Nos. 4,675,361 and 6,939,377, both of which are incorporated herein by reference. THORALON is a polyurethane base polymer blended (referred to as BPS-215) with a siloxane containing surface modifying additive (referred to as SMA-300). The concentration of the surface modifying additive may be in the range of 0.5% to 5% by weight of the base polymer.

The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

THORALON can be manipulated to provide either porous or non-porous THORALON. Porous THORALON can be formed by mixing the polyetherurethane urea (BPS-215), the surface modifying additive (SMA-300) and a particulate substance in a solvent. The particulate may be any of a variety of different particulates, pore forming agents or inorganic salts. Preferably the particulate is insoluble in the solvent. Examples of solvents include dimethyl formamide (DMF), tetrahydrofuran (THF), dimethyacetamide (DMAC), dimethyl sulfoxide (DMSO), or mixtures thereof. The composition can contain from about 5 wt % to about 40 wt % polymer, and different levels of polymer within the range can be used to fine tune the viscosity needed for a given process. The composition can contain less than 5 wt % polymer for some spray application embodiments. The particulates can be mixed into the composition. For example, the mixing can be performed with a spinning blade mixer for about an hour under ambient pressure and in a temperature range of about 18° C. to about 27° C. The entire composition can be cast as a sheet, or coated onto an article such as a mandrel or a mold. In one example, the composition can be dried to remove the solvent, and then the dried material can be soaked in distilled water to dissolve the particulates and leave pores in the material. In another example, the composition can be coagulated in a bath of distilled water. Since the polymer is insoluble in the water, it will rapidly solidify, trapping some or all of the particulates. The particulates can then dissolve from the polymer, leaving pores in the material. It may be desirable to use warm water for the extraction, for example water at a temperature of about 60° C. The resulting pore diameter can be substantially equal to the diameter of the salt grains.

The porous polymeric sheet can have a void-to-volume ratio from about 0.40 to about 0.90. Preferably the void-to-volume ratio is from about 0.65 to about 0.80. Void-to-volume ratio is defined as the volume of the pores divided by the total volume of the polymeric layer including the volume of the pores. The void-to-volume ratio can be measured using the protocol described in AAMI (Association for the Advancement of Medical Instrumentation) VP20-1994, Cardiovascular Implants—Vascular Prosthesis section 8.2.1.2, Method for Gravimetric Determination of Porosity. The pores in the polymer can have an average pore diameter from about 1 micron to about 400 microns. Preferably the average pore diameter is from about 1 micron to about 100 microns, and more preferably is from about 1 micron to about 10 microns. The average pore diameter is measured based on images from a scanning electron microscope (SEM). Formation of porous THORALON is described, for example, in U.S. Pat. No. 6,752,826 and U.S. Patent Application Publication No. 2003/0149471 A1, both of which are incorporated herein by reference.

Non-porous THORALON can be formed by mixing the polyetherurethane urea (BPS-215) and the surface modifying additive (SMA-300) in a solvent, such as dimethyl formamide (DMF), tetrahydrofuran (THF), dimethyacetamide (DMAC), dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments. The entire composition can be cast as a sheet, or coated onto an article such as a mandrel or a mold. In one example, the composition can be dried to remove the solvent.

THORALON has been used in certain vascular applications and is characterized by thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial.

A variety of other biocompatible polyurethanes may also be employed. These include polyurethane ureas that preferably include a soft segment and include a hard segment formed from a diisocyanate and diamine. For example, polyurethane ureas with soft segments such as polytetramethylene oxide, polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

The diisocyanate used as a component of the hard segment may be represented by the formula OCN—R—NCO, where —R— may be aliphatic, aromatic, cycloaliphatic or a mixture of aliphatic and aromatic moieties. Examples of diisocyanates include tetramethylene diisocyanate, hexamethylene diisocyanate, trimethyhexamethylene diisocyanate, tetramethylxylylene diisocyanate, 4,4'-decyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain oxygen and/or halogen atoms in their structures.

Other applicable biocompatible polyurethanes include those using a polyol as a component of the hard segment. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, neopentyl alcohol, 1,6-hexanediol, 1,8-octanediol, propylene glycols, 2,3-butylene glycol, dipropylene glycol, dibutylene glycol, glycerol, or mixtures thereof.

Biocompatible polyurethanes modified with cationic, anionic and aliphatic side chains may also be used. See, for example, U.S. Pat. No. 5,017,664.

Other biocompatible polyurethanes include: segmented polyurethanes, such as BIOSPAN; polycarbonate urethanes, such as BIONATE; and polyetherurethanes such as ELASTHANE; (all available from POLYMER TECHNOLOGY GROUP, Berkeley, Calif.).

Other biocompatible polyurethanes include polyurethanes having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Publication No. 2002/0187288 A1, published Dec. 12, 2002, which is incorporated herein by reference.

In addition, any of these biocompatible polyurethanes may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

In another embodiment of the invention, the valve leaflet material is formed from a polyparaxylene ("parylene") or a parylene derivative, for example parylene C or parylene N. For example, the parylene or parylene derivative is created by first heating p-xylene or a suitable derivative at an appropriate temperature (for example, at about 950° C.) to produce the cyclic dimer di-p-xylylene (or a derivative thereof). The resultant solid can be separated in pure form, and then cracked and pyrolyzed at an appropriate temperature (for example, at about 680° C.) to produce a monomer vapor of p-xylylene (or derivative); the monomer vapor is cooled to a suitable temperature (for example, below 50° C.) and the leaflet formed by vapor phase deposition.

Attachment of the Valve Leaflets to the Support Frame and Support Elements

Another aspect of the present invention provides methods for attaching a valve leaflet to the support frame and the support element(s). The valve leaflet material can be attached by any appropriate attachment means, including but not limited to, adhesive, fasteners, and tissue welding using heat and/or pressure. Alternatively, the valve leaflet may be formed on the support frame and support element(s) by an appropriate means, including but not limited to vapor deposition, spraying, electrostsatic deposition, ultrasonic deposition, or dipping.

For example, one edge of a sheet of leaflet material can be wrapped around a portion of the support frame and support element(s) and a small amount of a suitable solvent is then applied to the edge of the leaflet material to dissolve the edge into an adjacent portion of the leaflet material and thereby seal the material around the support frame and support element(s). In another embodiment, the sheet of leaflet material is shaped to form a leaflet and is attached to a portion of a support frame and support element(s) using stitching through the leaflet material and around a portion of the support frame and support element(s).

In one embodiment of the invention, the valve prosthesis includes a valve leaflet formed from a non-porous biocompatible polyurethane based polymer, such as non-porous THORALON. According to one method of attachment, a solution comprising a dissolved THORALON is coated and dried on a mandril to form a valve leaflet.

A solution for forming non-porous THORALON can be made by mixing the polyetherurethane urea (BPS-215) and the surface modifying additive (SMA-300) in a solvent, such as dimethyl formamide (DMF), tetrahydrofuran (THF), dimethyacetamide (DMAC), or dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments.

The entire composition can be cast as a sheet, or coated onto an article such as a mandril or a mold. In one example, the composition can be dried to remove the solvent. The mandril can be made from any suitable material that permits the THORALON to coated, dried on and removed from the mandril surface. Suitable materials include stainless steel and glass. In one embodiment, at least a portion of the outer surface of the mandril is formed in the desired shape of a valve leaflet. The valve leaflet can be formed by coating a thin layer of a solution of THORALON onto the shaped portion of the mandril, drying the coating of the THORALON on the mandril surface, and carefully removing the dried layer of THORALON.

One or more valve leaflets can be attached to the support frame by any suitable technique. In one embodiment, the valve leaflets include THORALON that is attached to the support frame by being formed around and encapsulating portions of the support frame. In one method, a solution comprising dissolved THORALON is sprayed and dried on an assembly formed by fitting at least a portion of the support frame over a mandril to form a valve prosthesis including one or more valve leaflets.

In one embodiment, one or more pre-coating layer(s) of THORALON are coated onto at least a portion of the mandril. The support frame is then fitted onto the mandril. The support frame can be any of those described above. A solution comprising a DMAC solution of non-porous THORALON is then coated onto the assembly comprising the mandril and the support frame using any suitable method, including spraying or dipping.

In one embodiment, a solution of THORALON is sprayed from a spray gun onto the assembly and the mandril is rotated during spraying process to promote uniform coating of the mandril. Any suitable rate of rotation can be used that provides for a uniform coating of the mandril and retains the coated material on the surface of the mandril. In one embodiment, the mandril is rotated at a rate of about 1 rpm.

When a pre-coating layer is present on the mandril, the THORALON adheres to the pre-coating layer as the solution of THORALON is spray coated onto the surface of the assembly and forms a sheet of THORALON that encapsulates portions of the support frame. Optionally, one or more bioactive agents can be coated onto the mandril with the THORALON.

In one embodiment, the pre-coating layer is first dried on the mandril, then the support frame is placed over the coated mandril, and finally second layer of THORALON is spray coated over the support frame as a solution comprising a suitable solvent such as DMAC and THORALON. The solvent in the spray solution preferably partially solubilizes the pre-coating layer so that one fused layer of THORALON is formed. The fused layer can encapsulate portions of the support frame and be solidified by evaporation of residual solvent, thereby joining the THORALON to the support frame. The residual solvent in the fused layer can be evaporated by heating the valve prosthesis on the mandril.

Alternatively, one or more valve leaflets can be attached to the support frame by other methods. In one embodiment, a sheet of material is cut to form a valve leaflet and the edges of the leaflet are wrapped around portions of a support frame and portions of the valve leaflet sealibly connected together to fasten the valve leaflet around the support frame. For example, one edge of a sheet of valve leaflet material can be wrapped around a portion of the support frame and held against the body of the valve leaflet, so that the valve leaflet material forms a lumen enclosing a portion of the support frame. A small amount of a suitable solvent is then applied to the edge of the valve leaflet material to dissolve the edge into an adjacent portion of the valve leaflet material and thereby seal the material around the support frame.

In another embodiment, the sheet of valve leaflet material is shaped to form the valve leaflet that is attached to a portion of a support frame using stitching through the valve leaflet material and around a portion of the support structure, adhesives, tissue welding or cross linking to directly join the valve leaflet material to the support frame. A valve leaflet attached to a support frame can be permitted to move relative to the support frame, or the valve leaflet can be substantially fixed in its position or orientation with respect to the support frame by using attachment configurations that resist relative movement of the valve leaflet and the support frame.

An electrostatic spray deposition (ESD) method of coating the valve leaflet material onto a mandril can also be used to form a valve leaflet. In this embodiment, particles in the sprayed solution of valve leaflet material are electrostatically charged when leaving the nozzle of the spray gun and the mandril is maintained at an electrical potential or grounded to attract the charged particles from the sprayed solution of valve leaflet material. The solution of valve leaflet material is first dissolved in a solvent and then sprayed onto the mandril using an ESD process.

The ESD process generally depends on the principle that a charged particle is attracted towards a grounded target. Without being confined to any theory, the typical ESD process may be described as follows. The solution that is to be deposited on the mandril is typically charged to several thousand volts (typically negative) and the mandril held at ground potential. The charge of the solution is generally great enough to cause the solution to jump across an air gap of several inches before landing on the target. As the solution is in transit towards the target, it fans out in a conical pattern which aids in a more uniform coating. In addition to the conical spray shape, the charged particles are further attracted towards the conducting portions of the target, rather than towards any non-conductive region of the target, leaving the coating mainly on the conducting regions of the target.

Generally, the ESD method allows for control of the coating composition and surface morphology of the deposited coating. In particular, the morphology of the deposited coating may be controlled by appropriate selection of the ESD parameters, as set forth in WO 03/006180 (Electrostatic Spray Deposition (ESD) of biocompatible coatings on Metallic Substrates), the contents of which are incorporated herein by reference. For example, a coating having a uniform thickness and grain size, as well as a smooth surface, may be obtained by controlling deposition conditions such as deposition temperature, spraying rate, precursor solution, and bias voltage between the spray nozzle and the medical device being coated. The deposition of porous coatings is also possible with the ESD method.

One hypothetical example of an electrostatic spraying apparatus and method is provided. Specifically, a solution of a non-porous THORALON material could be loaded into a 20 mL syringe of an ESD apparatus from Teronics Development Corp., which can then be mounted onto a syringe pump and connected to a tub that carries the solution to a spray head. The syringe pump could then used to purge the air from the solution line and prime the line and spray nozzle with solution. An electrical connection to the nozzle could supply the required voltage. An electrical connection could be provided to hold the mandril at grounding potential.

A motor could then be activated to rotate the mandril at a constant speed of about 1 rpm. The syringe pump could then be activated to supply the nozzle with a consistent flow of solution, and the power supply could be activated to provide a charge to the solution and cause the solution to jump the air gap and land on the mandril surface. As the coated surface is rotated away from the spray path, the volatile portion of the solution could be evaporated leaving a coating of THORALON behind. The mandril could be continually rotated in the spray pattern until the desired amount of non-porous THORALON material accumulates. During the coating process, the mandril could preferably be kept at ambient temperature and humidity, the solution could be pumped at a rate of about 2-4 $cm^3$/hr through the spray gun (which can be placed at a horizontal distance of approximately 6 cm from the mandril), and the bias voltage between the spray nozzle and the mandril should be approximately 10-17 kilovolts.

A support frame could then be slipped over a mandril (Teronics Development Corp., 2 mm×30 mm) so that at least a portion of the support frame makes an electrical connection with the mandril. The mandril could again be continually rotated in the spray pattern until the desired amount of non-porous THORALON material accumulates.

Where it is desired that portions of the perimeter of the valve leaflet material are not attached to the support frame, the valve leaflet material may be cut to free the material from the support frame. Alternatively, a mask may be used to cover portions of the support frame to prevent attachment of THORALON. The mask can be made from any suitable material that permits the THORALON to coated, dried on and removed from the mask surface. In one embodiment, a mask could be applied to the mandril surface before application of pre-coating layer(s) of THORALON. After the pre-coating layer(s) are applied, the mask could be removed and the support frame placed on the mandril. The mandril could again be continually rotated in the spray pattern until the desired amount of non-porous THORALON material accumulates. Only those portions of the support frame placed over portions of the mandril having a pre-coating of THORALON would be enclosed in THORALON.

Further examples of methods of preparation of valve prostheses, including methods of attaching a valve leaflet to a support frame, can be found in U.S. Publication No. 2004/0186558 A1, published Sep. 23, 2004, the contents of which are incorporated by reference.

Incorporation of Bioactive Agents

Valve prostheses of the present invention can include one or more bioactive agents. Bioactive agents can be included in any suitable part of the valve prosthesis, for example in the support frame, the support element(s) and/or the valve leaflet. Selection of the type of bioactive agent, the portions of the valve prosthesis comprising the bioactive agent and the manner of attaching the bioactive agent to the valve prosthesis can be chosen to perform a desired therapeutic function upon implantation and, in particular, to achieve controlled release of the bioactive agent.

For example, a therapeutic bioactive agent can be combined with a biocompatible polyurethane, impregnated in an extracellular collagen matrix material, incorporated in the support structure or coated over any portion of the valve prosthesis. In one embodiment, the valve prosthesis can comprise one or more valve leaflets comprising a bioactive agent coated on the surface of the valve leaflet or impregnated in the valve leaflet. In another aspect, a bioactive material is combined with a biodegradable polymer to form a portion of the support structure.

A bioactive agent can be incorporated in or applied to portions of the valve prosthesis by any suitable method that permits controlled release of the bioactive agent material and the effectiveness thereof for an intended purpose upon implantation in the body vessel. Preferably, the bioactive agent is incorporated into or coated onto the support frame and/or support element(s). The configuration of the bioactive agent on or in the valve prosthesis will depend in part on the desired rate of elution for the bioactive agent. Bioactive agents can be coated directly on the valve prosthesis surface or can be adhered to a valve prosthesis surface by means of a coating. For example, a bioactive agent can be blended with a polymer and spray or dip coated on the valve prosthesis surface. For example, a bioactive agent material can be posited on the surface of the valve prosthesis and a porous coating layer can be posited over the bioactive agent material. The bioactive agent material can diffuse through the porous coating layer. Multiple porous coating layers and or pore size can be used to control the rate of diffusion of the bioactive agent material. The coating layer can also be nonporous wherein the rate of diffusion of the bioactive agent material through the coating layer is controlled by the rate of dissolution of the bioactive agent material in the coating layer.

The bioactive agent material can also be dispersed throughout the coating layer, by for example, blending the bioactive agent with the polymer solution that forms the coating layer. If the coating layer is biostable, the bioactive agent can diffuse through the coating layer. If the coating layer is biodegradable, the bioactive agent is released upon erosion of the biodegradable coating layer.

Bioactive agents may be bonded to the coating layer directly via a covalent bond or via a linker molecule which covalently links the bioactive agent and the coating layer. Alternatively, the bioactive agent may be bound to the coating layer by ionic interactions including cationic polymer coatings with anionic functionality on bioactive agent, or alternatively anionic polymer coatings with cationic functionality on the bioactive agent. Hydrophobic interactions may also be used to bind the bioactive agent to a hydrophobic portion of the coating layer. The bioactive agent may be modified to include a hydrophobic moiety such as a carbon based moiety, silicon-carbon based moiety or other such hydrophobic moiety. Alternatively, the hydrogen bonding interactions may be used to bind the bioactive agent to the coating layer.

The bioactive agent can optionally be applied to or incorporated in any suitable portion of the valve prosthesis. The bioactive agent can be applied to or incorporated in the valve prosthesis, a polymer coating applied to the valve prosthesis, a material attached to the valve prosthesis or a material forming at least a portion of the valve prosthesis. The bioactive agent can be incorporated within the material forming the support frame, or within holes or wells formed in the surface of the support frame. The valve prosthesis can optionally comprise a coating layer containing the bioactive agent, or combinations of multiple coating layers configured to promote a desirable rate of elution of the bioactive from the valve prosthesis upon implantation within the body.

A coating layer containing a bioactive agent can include a bioactive agent and a biostable polymer, a biodegradable polymer or any combination thereof. In one embodiment, the bioactive agent is blended with a biostable polymer to deposit the bioactive agent within the porous channels within the biostable polymer that permit elution of the bioactive agent from the valve prosthesis upon implantation. Alternatively, a blend of the bioactive and the bioabsorbable polymer can be incorporated within a biostable polymer matrix to permit dissolution of the bioabsorbable polymer through channels or pores in the biostable polymer matrix upon implantation in the body, accompanied by elution of the bioactive agent.

Multiple coating layers can be configured to provide a valve prosthesis with a desirable bioactive agent elution rate upon implantation. The valve prosthesis can comprise a diffusion layer positioned between a portion of the valve prosthesis that comprises a bioactive agent and the portion of the valve prosthesis contacting the body upon implantation. For example, the diffusion layer can be a porous layer positioned on top of a coating layer that comprises a bioactive agent. The diffusion layer can also be a porous layer positioned on top of a bioactive agent coated on or incorporated within a portion of the valve prosthesis.

A porous diffusion layer is preferably configured to permit diffusion of the bioactive agent from the valve prosthesis at a desirable elution rate upon implantation within the body.

Prior to implantation, the diffusion layer can be substantially free of the bioactive agent. Alternatively, the diffusion layer can include a bioactive agent within pores in the diffusion layer. Optionally, the diffusion layer can include a mixture of a biodegradable polymer and a bioactive positioned within pores of a biostable polymer. In another embodiment, the porous diffusion layer can comprise a mixture of a biodegradable polymer and a biostable polymer, configured to permit absorption of the biodegradable polymer upon implantation of the valve prosthesis. The absorption of the biodegradable polymer forms one or more channels or pores in the biostable polymer, permitting diffusion of an underlying bioactive agent from the device.

In one embodiment, the valve prosthesis is coated with a coating of between about 1 μm and 50 μm, or preferably between 3 μm and 30 μm, although any suitable thickness can be selected. The coating can comprise a bioactive material layer contacting a separate layer comprising a carrier, a bioactive material mixed with one or more carriers, or any combination thereof. The carrier can be biologically or chemically passive or active, but is preferably selected and configured to provide a desired rate of release of the bioactive material. In one embodiment, the carrier is a bioabsorbable material, and one preferred carrier is poly-L-lactic acid. U.S. Publication No. 2004/0034409A1, published Feb. 19, 2004, describes methods of coating a bioabsorbable metal support frame with bioabsorbable materials such as poly-L-lactic acid that are incorporated herein by reference.

Medical devices including an antithrombogenic bioactive material are particularly preferred for implantation in areas of the body that contact blood. An antithrombogenic bioactive material is any bioactive material that inhibits or prevents thrombus formation within a body vessel. The medical device can include any suitable antithrombogenic bioactive material. Types of antithrombotic bioactive materials include anticoagulants, antiplatelets, and fibrinolytics. Anticoagulants are bioactive materials which act on any of the factors, cofactors, activated factors, or activated cofactors in the biochemical cascade and inhibit the synthesis of fibrin. Antiplatelet bioactive materials inhibit the adhesion, activation, and aggregation of platelets, which are key components of thrombi and play an important role in thrombosis. Fibrinolytic bioactive materials enhance the fibrinolytic cascade or otherwise aid is dissolution of a thrombus.

Examples of antithrombotics include, but are not limited to, anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic bioactive materials include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, Cl-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive materials such as endothelial progenitor cells or endothelial cells.

Other examples of bioactive coating compounds include antiproliferative/antimitotic agents including vinca alkaloids (vinblastine, vincristine, vinorelbine), paclitaxel, epidipodophyllotoxins (e.g. etoposide, teniposide), antibiotics, dactinomycin, actinomycin D, daunorubicin, doxorubicin, idarubicin, anthracyclines, mitoxantrone, bleomycins, plicamycin (mithramycin), mitomycin, enzymes (e.g. L-asparaginase which systemically metabolizes L-asparagine and deprives cells which do not have the capacity to synthesize their own asparagine); antiplatelet agents such as (GP) II$_b$/III$_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (e.g. fluorouracil, floxuridine, and cytarabine), purine analogs and related inhibitors (e.g. mercaptopurine, thioguanine, pentostatin and 2-chlorodeoxyadenosine (cladribine)); platinum coordination complexes (cisplatin, carboplatin), procarbazine, hydroxyurea, mitotane, aminoglutethimide; hormones (e.g. estrogen); anticoagulants (e.g. heparin, synthetic heparin salts and other inhibitors of thrombin); fibrinolytic agents (e.g. tissue plasminogen activator, streptokinase and urokinase), aspirin, dipyridamole, ticlopidine, clopidogrel, abciximab; an antimigratory; an antisecretory (breveldin); anti-inflammatory agents such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (e.g. cyclosporine, tacrolimus (FK-506), sirolimus (rapamycin), tacrolimus, everolimus, azathioprine, mycophenolate mofetil); angiogenic agents: vascular endothelial growth factor (VEGF), fibroblast growth factor (FGF); angiotensin receptor blockers; nitric oxide and nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; endothelial progenitor cells (EPC); angiopeptin; pimecrolimus; angiopeptin; HMG co-enzyme reductase inhibitors (statins); metalloproteinase inhibitors (batimastat); protease inhibitors; antibodies, such as EPC cell marker targets, CD34, CD133, and AC 133/CD133; Liposomal Biphosphate Compounds (BPs), Chlodronate, Alendronate, Oxygen Free Radical scavengers such as Tempamine and PEA/NO preserver compounds, and an inhibitor of matrix metalloproteinases, MMPI, such as Batimastat. Still other bioactive agents that can be incorporated in or coated on a frame include a PPAR α-agonist, a PPAR δ agonist and RXR agonists, as disclosed in published U.S. Publication No. 2004/0073297, published Apr. 15, 2004, and incorporated in its entirety herein by reference.

Device Delivery and Methods of Treatment

The valve prosthesis as described herein can be delivered to any suitable body vessel, including a vein, artery, biliary duct, ureteral vessel, body passage or portion of the alimentary canal. Methods for delivering a valve prosthesis as described herein to any suitable body vessel are also provided, such as a vein, artery, biliary duct, ureteral vessel, body passage or portion of the alimentary canal. While many preferred embodiments discussed herein discuss implantation of a valve prosthesis in a vein, other embodiments provide for implantation within other body vessels. In another matter of terminology there are many types of body canals, blood vessels, ducts, tubes and other body passages, and the term "vessel" is meant to include all such passages.

In some embodiments, valve prostheses of the present invention having a compressed delivery configuration with a very low profile, small collapsed diameter and great flexibility, may be able to navigate small or tortuous paths through a variety of body vessels. A low-profile valve prosthesis may also be useful in coronary arteries, carotid arteries, vascular aneurysms, and peripheral arteries and veins (e.g., renal, iliac, femoral, popliteal, sublavian, aorta, intercranial, etc.). Other nonvascular applications include gastrointestinal, duodenum, biliary ducts, esophagus, urethra, reproductive tracts, trachea, and respiratory (e.g., bronchial) ducts. These applications may optionally include a sheath covering the valve prosthesis. In one aspect, the valve prostheses described herein are implanted from a portion of a catheter inserted in a body vessel.

For example, a valve prosthesis can be compressed to a delivery configuration within a lumen enclosed by a retaining sheath that is part of a delivery system, such as a catheter-based system. Upon delivery, the valve prosthesis can be expanded, for example, by removing the retaining sheath, or portion thereof, and inflating a balloon from inside the valve prosthesis. In other embodiments, the valve prosthesis may be self-expanding. The delivery configuration can be maintained prior to deployment of the valve prosthesis by any suitable means, including a sheath, a suture, a tube or other restraining material around all or part of the compressed valve prosthesis, or by other methods.

Valve prostheses can be deployed in a body lumen by means appropriate to their design. For example, the valve prostheses can be adapted for deployment using conventional methods known in the art and employing percutaneous transluminal catheter devices. The valve prostheses are designed for deployment by any of a variety of in situ expansion means.

The valve prosthesis may be mounted onto a catheter that holds the valve prosthesis as it is delivered through the body lumen and then releases the valve prosthesis and allows it to self-expand into contact with the body lumen. This deployment is effected after the valve prosthesis has been introduced percutaneously, transported transluminally and positioned at a desired location by means of the catheter. The restraining means may comprise a removable sheath.

The self-expanding valve prosthesis according to the invention may be deployed according to well-known deployment techniques for self-expanding medical devices. The valve prosthesis is positioned at the distal end of a catheter with a lubricous sleeve placed over the valve prosthesis to hold the medical device in a contracted state with a relatively small diameter. The valve prosthesis may then be implanted at the point of treatment by advancing the catheter over a guidewire to the location of the lesion and then withdrawing the sleeve from over the valve prosthesis. The valve prosthesis will expand. The catheter, sleeve, and guidewire may then be removed from the patient.

For example, the support frame of the valve prosthesis is first positioned to surround a portion of an inflatable balloon catheter. The valve prosthesis, with the balloon catheter inside is configured at a first, collapsed diameter. The valve prosthesis and the inflatable balloon are percutaneously introduced into a body lumen, following a previously positioned guidewire in an over-the-wire angioplasty catheter system, and tracked by a fluoroscope, until the balloon portion and associated valve prosthesis are positioned within the body passageway at the point where the valve prosthesis is to be placed. Thereafter, the balloon is inflated and the valve prosthesis is expanded by the balloon portion from the collapsed diameter to a second expanded diameter. After the valve prosthesis has been expanded to the desired final expanded diameter, the balloon is deflated and the catheter is withdrawn, leaving the valve prosthesis in place. The valve prosthesis may be covered by a removable sheath during delivery to protect both the valve prosthesis and the vessels.

In certain configurations, a rapid exchange valve prosthesis delivery balloon catheter allows exchange from a balloon angioplasty catheter to a prosthesis delivery catheter without the need to replace the angioplasty catheter guide wire with an exchange-length wire guide before exchanging the catheters. Such delivery methods are described in U.S. Pat. Nos. 5,690,642, 5,814,061 and 6,371,961, the contents of which are incorporated by reference.

While the terms "contracted" and "compressed" have been used to describe the valve prosthesis as having the small diameter necessary for delivery to an implantation site, it will be appreciated that the terms, especially as applied to pressure-expandable valve prosthesis, should not be used to imply that the tube is under external pressure to provide the tube with a small diameter; i.e., a "contracted" or "compressed" pressure-expandable valve prosthesis may be formed and naturally reside in the "contracted" or "compressed" state until internally pressurized to expand. Therefore, "contracted" and "compressed" are intended only to imply that the valve prosthesis is in a state of having a small diameter relative to an expanded state. It will therefore be appreciated by those skilled in the art that yet other modifications could be made to the provided invention without deviating from its spirit and scope as so claimed.

In some embodiments, a bioabsorbable suture or sheath can be used to maintain a valve prosthesis in a compressed configuration both prior to and after deployment. As the bioabsorbable sheath or suture is degraded by the body after deployment, the valve prosthesis can expand within the body vessel. In some embodiments, a portion of the valve prosthesis can be restrained with a bioabsorbable material and another portion allowed to expand immediately upon implantation. For example, a self-expanding frame can be partially restrained by a bioabsorbable material upon deployment and later expand as the bioabsorbable material is absorbed.

Still other embodiments provide methods of treating a subject, which can be animal or human, including the step of implanting one or more valve prostheses as described herein. In some embodiments, methods of treating may also include the step of delivering a valve prosthesis to a point of treatment in a body vessel, or deploying a valve prosthesis at the point of treatment. Methods for treating certain conditions are also provided, such as venous valve insufficiency, varicose veins, esophageal reflux, restenosis or atherosclerosis. In some embodiments, the invention relates to methods of treating venous valve-related conditions.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously.

While the invention has been illustrated and described in detail in the drawings and foregoing description, the same is to be considered as illustrative and not restrictive in character, it being understood that only exemplary embodiments have been shown and described and do not limit the scope of the invention in any manner. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

We claim:

1. An artificial valve prosthesis for regulating fluid flow through a body vessel having a wall, comprising:
    an outer frame expandable between a first, unexpanded configuration and a second, fully expanded configuration, the outer frame having first and second outer frame ends, defining a circumference and forming a lumen extending between the first and second outer frame ends, the outer frame having an axial length extending from the first outer frame end to the second outer frame end and a uniform outer diameter along the axial length, the outer frame including a strut extending along the circumference;
    a first support element having a first end attached to the outer frame at a point on the circumference and extending radially inward from the point on the circumference to a second end disposed within the lumen, the second end defining a first commissural point;
    a first valve leaflet supported by the outer frame and by the first support element, the first valve leaflet having a perimeter and first and second portions of the perimeter, wherein the first portion of the perimeter of the first valve leaflet is continuously attached to the strut extending along the circumference such that the first portion of the perimeter extends continually along the circumference, and wherein a second portion of the perimeter of the first valve leaflet is continuously attached to the first support element extending from the point on the circumference to the first commissural point such that the second portion of the perimeter extends continually along the first support element from the point on the circumference to the first commissural point, and wherein the first valve leaflet is deformable between a first position allowing fluid flow in the first, antegrade direction and a second position restricting fluid flow in a second, retrograde direction,
    wherein the first support element allows for radial movement of the first commissural point with respect to the outer frame to accommodate restriction of retrograde fluid flow when said valve prosthesis is positioned within a body vessel of a size that prevents expansion of the outer frame to the fully expanded configuration.

2. The artificial valve prosthesis of claim 1, further comprising:
    a second valve leaflet supported by the outer frame and by the first support element, wherein the first and second valve leaflets are attached at the first commissural point and at a second commissural point, wherein the first and second valve leaflets co-apt between the first and second commissural points and wherein the first and second valve leaflets are deformable between a first position allowing fluid flow in the antegrade direction and a second position restricting fluid flow in the retrograde direction.

3. The artificial valve prosthesis of claim 2, wherein the second commissural point is positioned on the outer frame.

4. The artificial valve prosthesis of claim 1, wherein, when positioned within the body vessel, the portion of an edge of the valve leaflet supported by the first support element is not in contact with the wall of the vessel.

5. The artificial valve prosthesis of claim 2, further comprising: a second support element having a first end attached to the outer frame, wherein the second commissural point is positioned on the second support element.

6. The artificial valve prosthesis of claim 2, wherein the first valve leaflet and the second valve leaflet form a continuous piece of material.

7. The artificial valve prosthesis of claim 6, wherein the first and second support elements are reinforced portions of the continuous piece of material.

8. The artificial valve prosthesis of claim 1, wherein the outer frame comprises a polymeric material.

9. The artificial valve prosthesis of claim 1, wherein the outer frame comprises a material selected from a group consisting of stainless steel, nickel, silver, platinum, palladium, gold, titanium, tantalum, iridium, tungsten, a self-expanding nickel titanium alloy and inconel.

10. The artificial valve prosthesis of claim 9, wherein the outer frame comprises a self-expanding nickel titanium alloy.

11. The artificial valve prosthesis of claim 1, wherein the first valve leaflet comprises a material selected from the group consisting of a synthetic biocompatible polymer, cellulose acetate, cellulose nitrate, silicone, polyethylene, teraphthalate, polyurethane, polyamide, polyester, polyorthoester, poly anhydride, polyether sulfone, polycarbonate, polypropylene, high molecular weight polyethylene, a fluoroplastic material, polytetrafluoroethylene, polylactic acid, polyglycolic acid or copolymers thereof, a polyanhydride, polycaprolactone, polyhydroxy-butyrate valerate, polyhydroxyalkanoate, a polyetherurethane urea, naturally derived or synthetic collagenous material, an extracellular matrix material, submucosa, small intestinal submucosa, stomach submucosa, urinary bladder submucosa, uterine submucosa, renal capsule membrane, dura mater, pericardium, serosa, peritoneum or basement membrane materials, liver basement membrane and mixtures or copolymers thereof.

12. The artificial valve prosthesis of claim 1, where the first valve leaflet comprises a bioremodelable material.

13. The artificial valve prosthesis of claim 1, wherein the first valve leaflet comprises small intestinal submucosa.

14. The artificial valve prosthesis of claim 1, wherein the first valve leaflet comprises a polyurethane.

15. The artificial valve prosthesis of claim 2, wherein when the outer frame is in the expanded configuration, the first and second commissural points are separated by a distance less than a diameter of the outer frame.

16. The artificial valve prosthesis of claim 1, wherein the first support element comprises a polymeric material.

17. The artificial valve prosthesis of claim 1, wherein the first support element comprises a material selected from a group consisting of stainless steel, nickel, silver, platinum, palladium, gold, titanium, tantalum, iridium, tungsten, a self-expanding nickel titanium alloy, and inconel.

18. The artificial valve prosthesis of claim 1, further comprising a suture attaching the first support element to the outer frame.

19. The artificial valve prosthesis of claim 1, wherein at least 40% of the perimeter of the first valve leaflet is attached to the first support element.

20. The artificial valve prosthesis of claim 1, wherein the first portion and second portion of the perimeter of the first valve leaflet form an oblique angle in the perimeter at the point on the circumference at which that first end of the first support element is attached to the outer frame.

* * * * *